United States Patent
Brammer

(10) Patent No.: US 8,507,731 B2
(45) Date of Patent: Aug. 13, 2013

(54) HYDROFORMYLATION PROCESS USING A SYMMETRIC BISPHOSPHITE LIGAND FOR IMPROVED CONTROL OVER PRODUCT ISOMERS

(75) Inventor: Michael A. Brammer, Hurricane, WV (US)

(73) Assignee: Dow Technology Investments LLC

( * ) Notice: Subject to any disclaimer, the term of this patent is extended or adjusted under 35 U.S.C. 154(b) by 179 days.

(21) Appl. No.: 13/059,354

(22) PCT Filed: Aug. 11, 2009

(86) PCT No.: PCT/US2009/053333
§ 371 (c)(1),
(2), (4) Date: Feb. 16, 2011

(87) PCT Pub. No.: WO2010/021863
PCT Pub. Date: Feb. 25, 2010

(65) Prior Publication Data
US 2011/0144392 A1    Jun. 16, 2011

Related U.S. Application Data

(60) Provisional application No. 61/090,035, filed on Aug. 19, 2008.

(51) Int. Cl.
*C07C 45/50* (2006.01)

(52) U.S. Cl.
USPC ............................................. 568/454

(58) Field of Classification Search
USPC ............................................. 568/454
See application file for complete search history.

(56) References Cited

U.S. PATENT DOCUMENTS

| | | | |
|---|---|---|---|
| 3,527,809 A | 9/1970 | Pruett et al. |
| 4,148,830 A | 4/1979 | Pruett et al. |
| 4,169,861 A | 10/1979 | Hughes |
| 4,247,486 A | 1/1981 | Brewester et al. |
| 4,717,775 A | 1/1988 | Billig et al. |
| 4,737,588 A | 4/1988 | Billig et al. |
| 4,748,261 A | 5/1988 | Billig et al. |
| 4,769,498 A | 9/1988 | Billig et al. |
| 5,288,918 A | 2/1994 | Maher et al. |
| 5,717,126 A | 2/1998 | Paciello et al. |
| 5,741,945 A | 4/1998 | Bryant et al. |
| 5,929,289 A | 7/1999 | Abatjoglou et al. |
| 6,153,800 A | 11/2000 | Gelling et al. |
| 7,173,138 B2 | 2/2007 | Ahlers et al. |
| 7,674,937 B2 | 3/2010 | Tolleson et al. |
| 7,863,487 B2 | 1/2011 | Eisenschmid et al. |
| 7,872,156 B2 | 1/2011 | Liu et al. |
| 7,906,688 B2 | 3/2011 | Brammer et al. |
| 2006/0058558 A1 | 3/2006 | Jeon et al. |
| 2007/0123735 A1 | 5/2007 | Jeon et al. |

FOREIGN PATENT DOCUMENTS

FR    2717480    9/1995

OTHER PUBLICATIONS

Van Rooy et al., "Bulky Diphosphite-Modified Rhodium Catalysts: Hydroformylation and Characterization", Organometallics, 1996, 15, 835-847.
Steyer et al., "Bis-phosphites and bis-phosphinites based on distally-functionalised calix[4]arenes: coordination chemistry and use in rhodium-catalysed, low-pressure olefin hydroformylation", Dalton Transactions, 2005, 1301-1309.
Kunze et al., "Calix[4]arene-based Bis-phosphonites, Bis-phosphites, and Bis-O-acyl-phosphites as Ligands in the Rhodium(I)-catalyzed Hydroformylation of 1-Octene", Z. Anorg. Allg. Chem., 2002, 628, 779-787.
Semeril et al., "Highly Regioselective Hydroformylation with Hemispherical Chelators," Chemistry, A European Journal, 2008, 14, 7144-7155.
Puckette, "Halophosphite Ligands for the Rhodium Catalyzed Low-Pressure Hydroformylation Reaction", Eastman Chemical Company, (2007), pp. 31-38.
Yasuhiro et al., "Production of Aldehydes", Patent abstract of JP11-255696, Sep. 21, 1999.
Yasuhiro et al., "Production of Aldehydes", Patent abstract of JP11-246464, Sep. 14, 1999.

*Primary Examiner* — Sikarl Witherspoon
(74) *Attorney, Agent, or Firm* — Marie Zuckerman; Paul D. Hayhurst

(57) ABSTRACT

A process for hydroformylating an α-olefin to produce two or more aldehydes comprising a normal aldehyde and one or more iso-aldehydes with a target molar ratio of the normal aldehyde to one or more iso-aldehydes in a selectable range from 3/1 to 60/1. The process uses a transition metal-ligand complex catalyst comprising a symmetric calixarene bisphosphite ligand. The target N/I ratio is selected by controlling carbon monoxide partial pressure.

18 Claims, No Drawings

HYDROFORMYLATION PROCESS USING A SYMMETRIC BISPHOSPHITE LIGAND FOR IMPROVED CONTROL OVER PRODUCT ISOMERS

CROSS REFERENCE TO PRIOR APPLICATIONS

This application is a 371 of PCT/US2009/053333 filed Aug. 11, 2009, which claims the benefit of U.S. Provisional Application Ser. No. 61/090,035 filed Aug. 19, 2008.

FIELD OF THE INVENTION

This invention generally relates to an improved process for hydroformylating an α-olefin to produce two or more aldehydes comprising a normal aldehyde and one or more iso-aldehydes with a selectable molar ratio of the normal aldehyde to the one or more iso-aldehydes.

BACKGROUND OF THE INVENTION

A hydroformylation process comprises contacting under reaction conditions an olefinically-unsaturated compound with carbon monoxide and hydrogen in the presence of a catalyst to produce one or more aldehydes. For example, U.S. Pat. Nos. 4,148,830, 4,717,775, and 4,769,498 generally relate to hydroformylation processes using transition metal-organophosphorus ligand complex catalysts. Preferred transition metals include iron, ruthenium, osmium, cobalt, rhodium, iridium, nickel, palladium and platinum. Rhodium is a more preferred transition metal. Organophosphines and organophosphites are preferred organophosphorus ligands. Aldehydes produced by hydroformylation processes are also referred to as oxo aldehydes, which have a wide range of utility, for example, as intermediates for hydrogenation to aliphatic alcohols, for amination to aliphatic amines, for oxidation to aliphatic acids, and for aldol condensation to plasticizers.

A transition metal-organophosphorus ligand complex catalyst produces in the hydroformylation process generally an isomeric mixture comprising a linear (normal or n-) aldehyde and one or more branched (iso- or i-) aldehydes. A ratio of the n-aldehyde to the sum of the iso-aldehydes, calculated by molar or by weight, is often described as N/I selectivity or N/I ratio. Since all isomeric aldehydes produced from a given olefinically-unsaturated compound have an identical molecular weight, the molar N/I ratio is identical to the weight N/I ratio. For the purposes of this invention, an N/I selectivity of a catalyst refers to the N/I ratio obtained from hydroformylation of an alpha-olefin unless otherwise stated. A "high" N/I ratio refers to an isomer ratio of at least 15/1; while a "low" N/I ratio refers to an isomer ratio of less than 15/1.

An N/I ratio is informative in describing a relative amount of the n-aldehyde in an isomeric mixture; however, differences in N/I ratios are not as informative in describing differences in percentages of the one or more iso-aldehydes in different isomeric mixtures. For example, an isomeric mixture with an N/I ratio of 50/1 contains only about 1% more iso-aldehydes than an isomeric mixture with an N/I ratio of 100/1; while an isomeric mixture with an N/I ratio of 2/1 contains about 31% more iso-aldehydes than an isomeric mixture with an N/I ratio of 50/1. Therefore, both N/I ratios and percentages of individual aldehydes are used to describe aldehyde isomeric mixtures.

The organophosphorus ligand provides predominant control over the N/I ratio achievable by its corresponding rhodium complex catalyst. Rhodium complex catalysts of organomonophosphorus ligands generally produce N/I ratios below 15/1. For example, rhodium-triphenylphosphine ligand complex catalysts are known to produce a limited N/I ratio from about 6/1 to about 12/1 from an alpha-olefin, depending primarily on the molar ratio employed of triphenylphosphine to rhodium, with high N/I ratios achieved only with high molar ratios of triphenylphosphine to rhodium, for example, greater than 200/1. Rhodium-tri(2,4-di-tert-butylphenyl)phosphite complex catalyst produces even a narrower N/I ratio range of generally from 0.5/1 to 3/1 depending on the reaction conditions.

Rhodium complex catalysts of certain organopolyphosphite ligands produce N/I ratios above 15/1 in hydroformylation processes, and consequently, these catalysts are subjects of both industrial interests and academic studies. U.S. Pat. Nos. 4,769,498 and 4,748,261 exemplify such industrial interests, while a publication by Annemiek van Rooy et al. in *Organometallics* (1996, 15, 835-847) exemplifies such academic studies. The latter discloses 1-octene hydroformylation results using rhodium complex catalysts of bulky diphosphites (also known as bisphosphites), including ligands A, B and C represented by the following formulas:

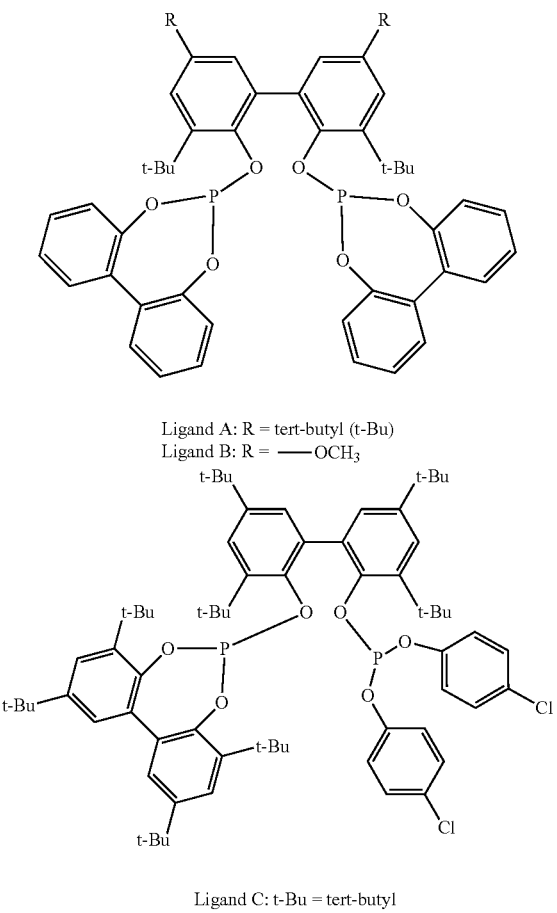

Ligand A: R = tert-butyl (t-Bu)
Ligand B: R = ——OCH₃

Ligand C: t-Bu = tert-butyl

The 1-octene hydroformylation results in the *Organometallics* publication include selectivity data towards normal and branched aldehydes using the rhodium complex catalysts of ligands A, B and C under specified reaction conditions (see Table 1 of the publication). The selectivity data translate to N/I ratios of greater than 51/1 from ligands A and B, and 19/1 from ligand C. The publication also reports that the selectivity for the normal aldehyde decreases with increasing carbon monoxide partial pressure when using the rhodium complex catalyst of ligand C (see Table 3 of the publication).

Ligands A and B, as free ligands, are symmetric with the two phosphites in each ligand being equivalent both electronically and sterically. Ligand C, in contrast, is unsymmetrical with one phosphite being less bulky than the other. Upon mixing with a source of transition metal, such as $Rh(CO)_2$acetylacetonate, the symmetric diphosphites give rise to chelating coordination immediately or after stirring for a few minutes, while the unsymmetrical diphosphite ligand C coordinates to the rhodium with its less bulky phosphite first and only forms chelating coordination after heating or evacuating to remove CO, as described in the *Organometallics* publication. The chelating coordination property of the symmetric diphosphites is preferred, because it enables a catalyst preparation by simply mixing the diphosphite and the source of transition metal. Symmetrical diphosphite ligands are preferred in commercial operations; see, for example, US Patent Publication 20060058558A1.

Substituted or unsubstituted biphenols are common linking groups for synthesizing diphosphites; see, for example ligands A, B and C hereinabove, and diphosphite ligands in U.S. Pat. Nos. 4,769,498 and 4,748,261. Derivatized calixarenes are also useful linking groups for synthesizing diphosphites to be used in hydroformylation processes. See, for example, U.S. Pat. No. 5,717,126 and unpublished International Application PCT/US2008/59216, filed on Apr. 3, 2008 in the name of Dow Global Technologies Inc. for "A CALIXARENE BISPHOSPHITE LIGAND FOR USE IN HYDROFORMYLATION PROCESSES," as well as publications by S. Steyer, et al., *Dalton Transactions*, 2005, 1301-1309; and C. Kunze, et al., *Z. Anorg. Allg. Chem.*, 2002, 628, 779-787.

By far the most important oxo chemical is n-butyraldehyde with world wide annual consumption of more than 50% of all oxo aldehydes by weight, based on the total weight of all oxo aldehydes consumed. Although world wide annual consumption of iso-butyraldehyde is only about 15% of that of n-butyraldehyde, at certain times in a chemical market cycle, it may be desirable to increase production of iso-butyraldehyde and decrease production of n-butyraldehyde of an oxo aldehyde plant. It is therefore desirable to have a hydroformylation process that produces two or more aldehydes with a selectable N/I ratio by controlling processing parameters.

To satisfy the ever changing market demands for isobutyraldehyde and n-butyraldehyde, the art teaches using a mixture of two ligands—a high N/I ligand, for example, a diphosphite, and a low N/I ligand, for example, a monophosphite, to carry out the hydroformylation process. See, for example, US Patent Application Publication 20070123735A1 and unpublished International Application PCT/US2008/056602, filed on Mar. 12, 2008 in the name of Union Carbide Chemicals & Plastics Technology LLC for "HYDROFORMYLATION PROCESS WITH IMPROVED CONTROL OVER PRODUCT ISOMERS."

SUMMARY OF THE INVENTION

The present invention provides a hydroformylation process for producing two or more aldehydes comprising a normal aldehyde and one or more iso-aldehydes with a target N/I ratio, which N/I ratio is defined as a molar ratio of the normal aldehyde to the one or more iso-aldehydes, the process comprising contacting under reaction conditions an α-olefin represented by formula (I):

$$R-CH_2-CH=CH_2 \quad (I)$$

wherein R is selected from the group consisting of hydrogen, substituted and unsubstituted $C_{1-9}$-alkyl moieties, with carbon monoxide and hydrogen in a reaction medium that is essentially free of an iso-olefin represented by formula (II):

$$R-CH_2-C(CH_3)=CH_2 \quad (II)$$

wherein R is as defined above, in the presence of a transition metal-ligand complex catalyst comprising a symmetric calixarene bisphosphite ligand represented by formula (III):

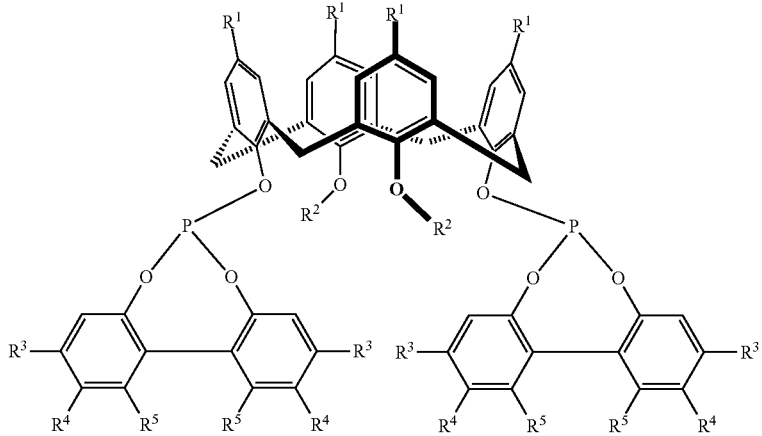

wherein each $R^1$ is the same and is selected from the group consisting of hydrogen and substituted or unsubstituted alkyl moieties;

wherein each $R^2$ is the same and is selected from the group consisting of substituted and unsubstituted alkyl, alkaryl, aralkyl, and amide moieties; and wherein each $R^3$ is the same, each $R^4$ is the same, and each $R^5$ is the same, and wherein $R^3$, $R^4$, and $R^5$ are independently selected from hydrogen, alkyl, alkaryl, alkoxy, aryloxy, keto, carbonyloxy, and alkoxycarbonyl moieties;

which contacting occurs under a carbon monoxide partial pressure in a range from 6 psi (41 kPa) to 300 psi (2.1 mPa) to produce the two or more aldehydes with the target N/I ratio, which target N/I ratio is selectable over a range from 3 to 60 by controlling the carbon monoxide partial pressure.

DETAILED DESCRIPTION OF THE INVENTION

As summarized hereinabove, the present invention provides a hydroformylation process for producing two or more aldehydes with a target N/I ratio selectable in a range from 3 to 60. The process comprises contacting an α-olefin of formula (I) with carbon monoxide and hydrogen in the presence of a transition metal-ligand complex catalyst wherein the ligand comprises a symmetric calixarene bisphosphite ligand of formula (III) shown hereinabove. The contacting occurs in a reaction medium that comprises the α-olefin, the transition metal-calixarene bisphosphite ligand complex catalyst, and optionally, free calixarene bisphosphite ligand and an organic solvent. The reaction medium is essentially free of an iso-olefin of formula (II) hereinabove. As discussed in detail hereinafter, the N/I ratio is controlled by varying carbon monoxide partial pressure.

As used herein, certain phrases, terms, and words are used that are defined herein. When interpreting a meaning of a phrase, term, or word, its definition herein governs unless, for a particular use, a different meaning is stated elsewhere in this specification or unless a context of the use of the phrase, term, or word clearly indicates a different meaning is intended from the definitions provided here.

The articles "a" and "the" refer to singular and plural forms of what is being modified by the articles. When used in front of a first member of a list of two or more members, the words "a" and "the" independently refer to each member in the list. As used herein, "a," "an," "the," "at least one," and "one or more" are used interchangeably. The term "comprises" and variations thereof do not have a limiting meaning where these terms appear in the description and claims. Thus, for example, a reactant mixture that comprises "a" ligand can be interpreted to mean that the ligand includes "one or more" ligands.

All percentages, preferred amounts or measurements, ranges and endpoints thereof herein are inclusive, that is, "a range from 5 to 10" includes 5 and 10. "At least" is equivalent to "greater than or equal to," and "at most" is, thus, equivalent to "less than or equal to." Numbers herein have no more precision than stated. Thus, "115" includes at least from 114.6 to 115.4. All ranges from a parameter described as "at least," "greater than," "greater than or equal to" or similarly, to a parameter described as "at most," "up to," "less than," "less than or equal to" or similarly are preferred ranges regardless of the relative degree of preference indicated for each parameter. Thus a range that has an advantageous lower limit combined with a most preferred upper limit is preferred for the practice of this invention. The term "advantageously" is used to denote a degree of preference more than required, but less than is denoted by the term "preferably."

Except in the examples, or where otherwise indicated, all numbers expressing quantities, percentages, properties, functionalities and so forth in the specification are to be understood as being modified in all instances by the term "about." Unless stated otherwise, when an element, material, or step capable of causing undesirable effects is present in amounts or in a form such that it does not cause the effect to an unacceptable degree, that element, material, or step is considered substantially absent for the practice of this invention. Those skilled in the art recognize that acceptable limits vary with equipment, conditions, applications, and other variables, but are determinable without undue experimentation in each situation where they are applicable. In some instances, variation or deviation in one parameter is acceptable to achieve another desirable end.

The relevant teachings of each reference cited herein are incorporated to the maximum extent allowed by United States law. In the event of a conflict between a portion of an incorporated reference and this Application, this Application takes precedence over the incorporated portion.

As used herein, the phrase "having the formula" or "represented by the formula" is not intended to be limiting and is used in the same manner as the term "comprising" is commonly used.

The term "alkyl" is defined as a univalent moiety derived from an alkane by removal of one hydrogen atom from one carbon atom. The alkane can be a linear or branched alkane and advantageously, although not necessarily, contains 1 to 20 carbon atoms, for example, methyl, ethyl, n-propyl, isopropyl, n-butyl, t-butyl, octyl, decyl, and the like. The alkane can also be a cycloalkane that advantageously contains from 4 to 8 carbon atoms, such as cyclopentane, cyclohexane, and cyclooctane. The term "substituted alkyl" refers to any one of the aforementioned alkyl groups substituted with one or more substituents as noted hereinafter.

The term "alkoxy" is defined as a univalent moiety represented by —O-alkyl, wherein alkyl is as defined hereinabove.

The term "aryl" is defined as a univalent moiety derived from an arene by removal of one hydrogen atom from one carbon atom. The arene can contain a single aromatic ring or multiple aromatic rings that are fused together, directly linked, or indirectly linked (such that the different aromatic groups are bound to a common group such as a methylene or ethylene moiety). Preferred aryl groups contain one aromatic ring, or 2 to 4 fused or linked aromatic rings, for example, phenyl, naphthyl, biphenyl, and the like. The term "substituted aryl" refers to an aromatic group substituted with one or more substituents as noted hereinafter.

The term "aryloxy" is defined as a univalent moiety represented by —O-aryl, where "aryl" is as defined hereinabove.

The term "aralkyl" or "arylalkyl" refers to an alkyl group having one or more aryl substituents.

The term "alkaryl" or "alkylaryl" refers to an aryl group having one or more alkyl substituents.

The term "alicyclic" refers to an aliphatic cyclic moiety, which can be monocyclic, bicyclic, or polycyclic.

The number of carbon atoms or a range thereof forming a moiety or compound is defined by prefixing the moiety or compound with a formula "$C_m$" or "$C_{m\text{-}n}$," respectively, wherein m and n are integers. For example, a $C_4$ alkane means the alkane has 4 carbon atoms, while a $C_{1\text{-}20}$ alkyl means the alkyl has a number of carbon atoms in the range from 1 to 20 carbon atoms.

The word "substituents" or "substituted" as used herein include, without limitation, functional groups such as halogen, phosphonato, phosphoryl, phosphine, sulfinato, $C_{1\text{-}20}$ alkylsulfanyl, $C_{5\text{-}20}$ arylsulfanyl, $C_{1\text{-}20}$ alkylsulfonyl, $C_{5\text{-}20}$ arylsulfonyl, $C_{1\text{-}20}$ alkylsulfinyl, $C_{5\text{-}20}$ arylsulfinyl, sulfonamide, amino, amido, imino, nitro, nitroso, hydroxyl, $C_{1\text{-}20}$ alkoxy, $C_{5\text{-}20}$ aryloxy, $C_{2\text{-}20}$ alkoxycarbonyl, $C_{5\text{-}20}$ aryloxycarbonyl, carboxylate, mercapto, formyl, $C_{1\text{-}20}$ thioester, cyano, cyanato, carbamoyl, epoxy, styrenyl, silyl, silyloxy, silanyl, siloxazanyl, and the hydrocarbyl moieties $C_{1\text{-}20}$ alkyl, $C_{2\text{-}20}$ alkenyl, $C_{2\text{-}20}$ alkynyl, $C_{5\text{-}20}$ aryl, $C_{5\text{-}30}$ aralkyl, and $C_{5\text{-}30}$ alkaryl.

The term "amide" refers to substituents of the formula —C(O)NR$^6$R$^7$ or —CH$_2$C(O)NR$^6$R$^7$, wherein R$^6$ and R$^7$ are each independently selected from substituted and unsubstituted alkyl and aryl moieties, more preferably, substituted and unsubstituted $C_{1\text{-}15}$ alkyl moieties and $C_{6\text{-}25}$ aryl moieties.

The term "carbonyloxy" refers to a substituent of the formula —OC(O)R$^8$, such as acetoxy for —OC(O)CH$_3$, wherein R$^8$ is a substituted or unsubstituted $C_{1\text{-}15}$ alkyl or $C_{6\text{-}15}$ aryl moiety.

The term "alkoxycarbonyl" refers to a substituent of the formula —C(O)OR$^8$ such as methoxycarbonyl for —C(O)OCH$_3$, wherein R$^8$ is a substituted or unsubstituted C$_{1-15}$ alkyl or C$_{6-15}$ aryl moiety.

The term "keto" refers to a —C(O)R$^8$ group, wherein R$^8$ is a substituted or unsubstituted C$_{1-15}$ alkyl or C$_{6-15}$ aryl moiety.

The term "optional" or "optionally" means that the subsequently described circumstance may or may not occur. For example, the term "optionally substituted" means that a non-hydrogen substituent may or may not be present on a given atom, and thus, the description includes structures wherein a non-hydrogen substituent is present and structures wherein a non-hydrogen substituent is not present.

Abbreviations and symbols "cony," "g," "hr," "L," "ml," "mol," "mmol," "M," "mM," "kPa," "mPa," "psi," "rpm," "° C.," and "%" are used, respectively, for "conversion," "gram," "hour" "liter," "milliliter," "mole," "millimole," "moles/liter," "millimole/liter," "kilo Pascal," "mega Pascal," "pounds per square inch," "revolutions per minute," "degree Celsius," and "percent," respectively, and plural forms thereof. All pressures are expressed as absolute pressures.

The term "syngas" refers to a mixture of carbon monoxide (CO) and hydrogen (H$_2$) in 1:1 molar ratio.

The symmetric calixarene bisphosphite ligand is selected from compounds represented by formula (III), reproduced hereinafter:

(III)

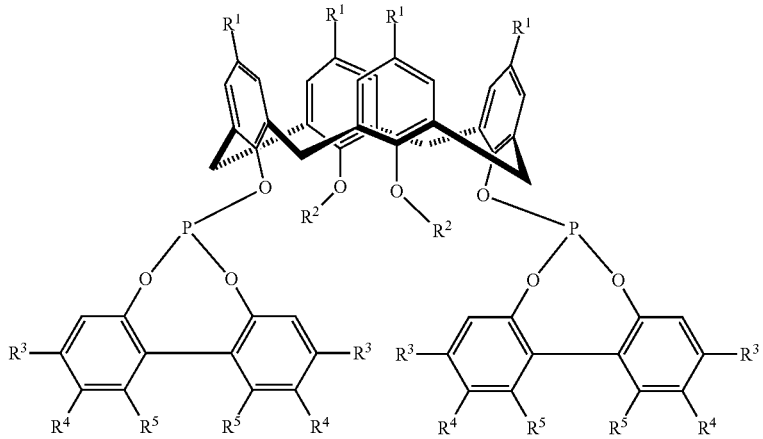

wherein R$^1$ through R$^5$ are as defined in the Summary of the invention. Preferably, individually or in any combination, R$^1$ through R$^5$ are selected as follows:

each R$^1$ is the same and is a C$_{1-20}$ alkyl;

each R$^2$ is the same and is selected from the group consisting of C$_{1-20}$ alkyl, C$_{7-20}$ alkaryl, and —CH$_2$C(O)NR$^6$R$^7$, wherein R$^6$ and R$^7$ are independently selected from substituted and unsubstituted C$_{1-15}$ alkyl moieties and C$_{6-25}$ aryl moieties, and/or each R$^3$ is the same, each R$^4$ is the same, and each R$^5$ is the same, and wherein R$^3$, R$^4$, and R$^5$ are independently selected from hydrogen, C$_{1-20}$ alkyl, C$_{7-20}$ alkaryl, C$_{1-20}$ alkoxy, C$_{6-20}$ aryloxy, —C(O)R$^8$, —C(O)OR$^8$ and —OC(O)R$^8$, wherein each R$^8$ is independently selected from substituted and unsubstituted C$_{1-15}$ alkyl moieties and C$_{6-15}$ aryl moieties.

More preferably, the symmetric calixarene bisphosphite ligand is N,N-diethylacetamide-p-tert-butylcalix[4]arene bisphosphite, which is represented by the following formula (IV):

(IV)

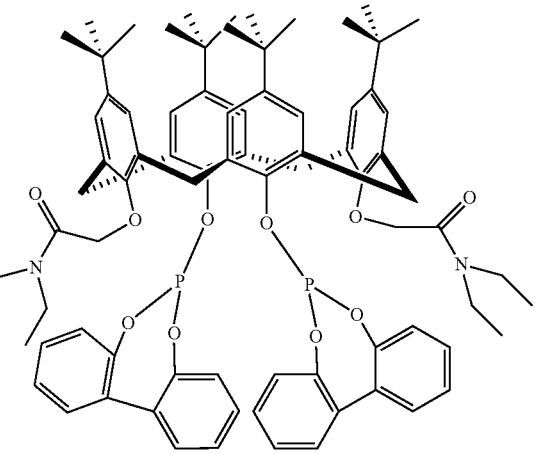

As a further option, the hydroformylation process of this invention can be conducted in the presence of free symmetric calixarene bisphosphite ligand, that is, ligand not complexed to the transition metal. The free symmetric calixarene bisphosphite ligand can correspond to any of the symmetric calixarene bisphosphite ligand species illustrated hereinabove. While it is preferred to employ a free symmetric calixarene bisphosphite ligand that is identical to the symmetric calixarene bisphosphite ligand complexed to the transition metal to form the transition metal-ligand complex catalyst, it is not required for the free and complexed symmetric calixarene bisphosphite ligands to be the same; and in fact, they can be different. Advantageously, the process employs an amount of the symmetric calixarene bisphosphite ligand sufficient to provide a molar ratio of the symmetric calixarene bisphosphite ligand to the transition metal present in the reaction medium of at least 1.0/1, preferably at least 1.2/1, and more preferably at least 1.5/1. Advantageously, the molar ratio of the symmetric calixarene bisphosphite ligand to the transition metal is less than 100/1, preferably less than 50/1, and more preferably less than 10/1. The aforementioned ratios correspond to the sum of both free and complexed calixarene bisphosphite ligand. Make-up calixarene bisphosphite ligand can be added during the process at any time and in any suitable manner, so as to maintain substantially a predetermined concentration of free ligand in the reaction medium.

The hydroformylation process is conducted by employing a transition metal-ligand complex catalyst or catalyst precursor, which comprises a transition metal and the symmetric calixarene bisphosphite ligand. The transition metal is advantageously selected from the group consisting of rhodium (Rh), cobalt (Co), iridium (Ir), ruthenium (Ru), iron (Fe), nickel (Ni), palladium (Pd), platinum (Pt), and osmium (Os), and mixtures thereof, preferably selected from the group consisting of palladium, platinum, rhodium, cobalt, and iridium, more preferably selected from the group consisting of rhodium and cobalt, and still more preferably rhodium. The term "complex" as used herein means a coordination compound formed by the union of one or more ligands, in this instance, at least one symmetric calixarene bisphosphite ligand, with a transition metal. Inherently, the symmetric calixarene bisphosphite ligand is more electron-rich than the transition metal, since each ligand possesses two phosphorus (III) donor atoms, each of which possesses one available or unshared pair of electrons that is capable of forming a coordinate bond independently or simultaneously (e.g., via chelation) with the transition metal. The oxidation state of the metal can be any available oxidation state, either electronically neutral (zero) or electronically deficient (positive valence) that allows for bonding to the symmetric calixarene bisphosphite ligand. Moreover, the oxidation state of the transition metal, as well as the overall charges of the coordination complex or complex precursor, can vary during use in the hydroformylation process. The number of available coordination sites on the transition metal is well known in the art and can range typically from 4 to 6. Optionally, carbon monoxide and hydrogen can be bonded to the transition metal.

Any amount of the transition metal-ligand complex catalyst can be employed in the hydroformylation reaction medium, provided that the amount is sufficient to catalyze the desired hydroformylation reaction to produce two or more aldehydes comprising a normal aldehyde and one or more iso-aldehydes having a target N/I ratio selectable in a range from advantageously 3, preferably 4, to advantageously 60, preferably 50. Advantageously, the concentration of complex catalyst provides for a concentration of transition metal of greater than 10 parts per million by weight (ppmw), preferably greater than 15 ppmw, and more preferably greater than 20 ppmw calculated as free metal, based on the total weight of the hydroformylation reaction medium. Advantageously, the concentration of complex catalyst provides for a concentration of transition metal of less than 1,000 ppmw, preferably less than 800 ppmw, and more preferably less than 600 ppmw, calculated as free metal, based on the total weight of the hydroformylation reaction medium.

The transition metal-ligand complex catalyst comprising the symmetric calixarene bisphosphite ligand of this invention can be prepared by methods known in the art. In one instance, the transition metal-ligand complex catalyst is preformed and introduced into the reaction medium or a reaction zone. The complex catalyst or catalyst precursor composition and its ligand components can be identified by standard identification methods, including for example, elemental analysis, mass spectroscopy, infrared spectroscopy, $^1H$, $^{31}P$, and/or $^{13}C$ nuclear magnetic resonance (NMR) spectroscopy, or a combination thereof.

Preferably, the symmetric calixarene bisphosphite ligand and a transition metal, preferably rhodium, source material are introduced into the reaction medium or zone, either separately or together, to form in situ the transition metal-ligand complex catalyst. Examples of rhodium source materials include, but are not limited to, rhodium acetylacetonate, rhodium dicarbonyl acetylacetonate ($Rh(CO)_2acac$), $Rh_2O_3$, $Rh_4(CO)_{12}$, $[RhCl(CO)_2]_2$, $Rh_6(CO)_{16}$, and $Rh(NO_3)_3$. In a preferred embodiment, the rhodium complex catalyst is prepared by the steps of:

a) charging the symmetric calixarene bisphosphite, a rhodium source material, for example $Rh(CO)_2acac$, with a molar ratio of the symmetric calixarene bisphosphite to rhodium in a range described hereinabove, for example from 1.0/1 to 100/1, and an organic solvent into the reaction medium or zone, either separately or together, to form a mixture, and b) subjecting the mixture to reaction conditions to form the active catalyst.

The reaction conditions sufficient for formation of the complex catalyst or catalyst precursor in most cases are similar to the hydroformylation reaction conditions described hereinbelow.

Although the symmetric calixarene bisphosphite ligand forms chelating coordination complexes readily when mixed with a transition metal source material, it is to be noted that successful practice of this hydroformylation process invention does not depend and is not predicated upon the exact formula of the catalytically active metal-ligand complex species, which can be present in a mononuclear, dinuclear, or higher nuclearity form. Indeed, the exact formula of the catalytically active metal-ligand complex can be difficult to determine analytically. Although not intended to be bound to any theory or mechanistic discourse, it appears that the active catalytic species in its general form comprises the transition metal in complex combination with at least one calixarene bisphosphite ligand of formula (III), further in combination with carbon monoxide. The catalytically active composition can also contain one or more additional ligands, such as hydrogen, or an anion satisfying the coordination sites or nuclear charge of the transition metal. Illustrative additional ligands include alkyl, aryl, substituted aryl, $CF_3^-$, $C_2F_5^-$, $CN^-$, $R'_2PO^-$, $R'P(O)(OH)O^-$ (wherein each R' is alkyl or aryl), $CH_3C(O)O^-$, acetylacetonate, $SO_4^{2-}$, $PF_4^-$, $PF_6^-$, $NO_2^-$, $NO_3^-$, $CH_3O^-$, $CH_2=CHCH_2^-$, $C_6H_5CN$, $CH_3CH=$, NO, $NH_3$, pyridine, $(C_2H_5)_3N$, mono-olefins, di-olefins, tri-olefins, and tetrahydrofuran.

The hydroformylation process employs advantageously an olefin feed that comprises primarily an α-olefin of formula (I) as defined hereinabove and is essentially free of an iso-olefin of formula (II) as defined hereinabove. The olefin feed comprises preferably at least 90%, more preferably at least 95% of the α-olefin by weight, based on the weight of the olefin feed. Other components in the α-olefin feed include alkanes, internal olefins, or mixtures thereof, which alkanes and internal olefins preferably have similar molecular weight as the α-olefin. For purposes of this invention, the term "essentially free of an iso-olefin" means that the iso-olefin is present, if at all, in an amount less than 0.4 weight percent, preferably less than 0.3 weight percent, based on the weight of the olefin feed, wherein the numbers of 0.4 and 0.3 are not to be modified by the term "about." Preferably, the α-olefin is selected from the group consisting of propene, 1-butene, 1-pentene, 4-penten-1-ol, 1-hexene, 1-heptene, 1-octene, 1-nonene, 1-decene, 1-undecene, 1-dodecene, and methyl 10-undecenoate.

The hydroformylation process of this invention is preferably conducted in the presence of an organic solvent. Any organic solvent can be employed so long as the organic solvent does not unduly interfere with the hydroformylation reaction. By way of illustration, suitable organic solvents for rhodium catalyzed hydroformylation processes include those disclosed, for example, in U.S. Pat. Nos. 3,527,809; 4,148, 830; and 5,929,289. Non-limiting examples of suitable organic solvents include saturated hydrocarbons, aromatic hydrocarbons, ethers, aldehydes, ketones, nitriles, and aldehyde condensation products. More specific examples of suitable organic solvents include, but are not limited to, tetraglyme, pentanes, cyclohexane, benzene, xylene, toluene, diethyl ether, tetrahydrofuran, butyraldehyde, benzonitrile, and mixtures thereof. Preferably, the organic solvent is a mixture that comprises primarily the aldehyde products desired to be produced in the process and/or higher boiling aldehyde liquid condensation by-products, for example, as can be produced in situ during the hydroformylation process, as described for example in U.S. Pat. Nos. 4,148,380 and 4,247,486. Indeed, while a continuous process can employ, if desired, any suitable solvent at the start-up of the process, the solvent will normally eventually comprise both aldehyde products and higher boiling aldehyde liquid condensation by-products, due to the nature of such continuous processes. The process employs the solvent in an amount sufficient to provide the reaction medium with the desired amount of transition metal concentration within the ranges described hereinabove. The amount of solvent advantageously is more than 5 percent, preferably more than 10 percent, more preferably more than 15 percent, and advantageously is less than 95 percent, preferably less than 90 percent, more preferably less than 85 percent, by weight, based on the total weight of the hydroformylation reaction medium.

The hydroformylation process produces the two or more aldehydes with a target N/I ratio selectable over a range from advantageously 3, preferably 4, to advantageously 60, preferably 50, by controlling the carbon monoxide partial pressure. The carbon monoxide partial pressure advantageously is at least 6 psi (41 kilo Pascal (kPa)), preferably at least 12 psi (83 kPa), and advantageously is less than 300 psi (2.1 mega Pascal (mPa)), and preferably less than 260 psi (1.8 mPa). The N/I ratio is inversely correlated to the carbon monoxide partial pressure over the above stated ranges, such that as the carbon monoxide partial pressure increases, the N/I ratio decreases, and as the carbon monoxide partial pressure decreases, the N/I ratio increases. The carbon monoxide partial pressure can be controlled within the aforementioned range either directly or indirectly. Direct CO control relies upon manipulation of an independent CO feed to the process; whereas indirect CO control relies upon manipulation of the hydrogen partial pressure, the syngas partial pressure, or the total pressure, as described hereinafter.

In a first preferred embodiment, each gaseous component (particularly, olefin, CO, $H_2$) of the hydroformylation process is preferably fed into the reactor independently at a target partial pressure for each component, which is any operable partial pressure that produces the two or more aldehydes with a target N/I ratio within the broad range specified in this invention. The target N/I ratio is then further selected and varied within this range by varying the carbon monoxide partial pressure alone, within the range from 6 psi (41 kPa) to 300 psi (2.1 mPa). Partial pressures of other gaseous components, such as hydrogen and the olefin feed, are preferably maintained within 90%, preferably within 95% of their respective target partial pressures. In this first preferred embodiment, the hydroformylation process employs a hydrogen partial pressure sufficient to produce the two or more aldehydes with the target N/I ratio over the ranges stated above. The hydrogen partial pressure advantageously is at least 6 psi (41 kPa), preferably at least 12 psi (83 kPa), and advantageously is less than 300 psi (2.1 mPa), and preferably less than 260 psi (1.8 mPa). The molar ratio of gaseous hydrogen to carbon monoxide advantageously is greater than 1/4, preferably greater than 1/2, more preferably equal to or greater than 1/1, and advantageously is less than 4/1, preferably less than 2/1, and more preferably equal to or less than 1/1.

In a second preferred embodiment, all gaseous components, such as hydrogen, carbon monoxide, and olefin feedstock, of the hydroformylation process are preferably fed into the reactor together to obtain the two or more aldehydes with a target N/I ratio. The target N/I ratio is further selected and varied by controlling the total gas pressure of all the gaseous components while keeping the relative ratios of the gaseous components essentially unchanged, which effectively controls the carbon monoxide partial pressure in the reactor. In this method the total gas pressure advantageously is at least 15 psi (103 kPa), preferably at least 30 psi (207 kPa), and advantageously is less than 650 psi (4.5 mPa), preferably less than 600 psi (4.1 mPa). The carbon monoxide and hydrogen partial pressures are selected as in the first preferred embodiment. In this second preferred embodiment, the hydroformylation process employs a molar ratio of gaseous hydrogen to carbon monoxide sufficient to produce the two or more aldehydes with the target N/I ratio over the ranges stated above. Again, the molar ratio of gaseous hydrogen to carbon monoxide advantageously is greater than 1/4, preferably greater than 1/2, more preferably equal to or greater than 1/1, and advantageously is less than 4/1, preferably less than 2/1, and more preferably equal to or less than 1/1.

In a third preferred embodiment, the hydroformylation process is preferably carried out by using syngas ($CO:H_2=1:1$) to obtain the two or more aldehydes with a target N/I ratio. The target N/I ratio is preferably selected by controlling the syngas pressure, which effectively controls the carbon monoxide partial pressure in the reactor. The syngas pressure advantageously is at least 12 psi (83 kPa), preferably at least 24 psi (166 kPa), and advantageously is less than 600 psi (4.1 mPa), preferably less than 500 psi (3.4 mPa).

In each of the above preferred embodiments, the target N/I ratio selectable over the range stated hereinabove can be further controlled by varying reaction temperature, the variation dependent on the selection of the α-olefin. The reaction temperature advantageously is greater than 60° C., preferably greater than 65° C., and is advantageously less than 110° C., and preferably less than 100° C. With certain olefin feeds, such as 1-butene, the N/I ratio is inversely correlated to the reaction temperature over the above stated ranges, such that as reaction temperature increases, the N/I ratio decreases, and as reaction temperature decreases, the N/I ratio increases.

The hydroformylation process of this invention can be carried out in the liquid or gas phase, or preferably, in mixed liquid and gas phases, which can more preferably involve a continuous liquid phase containing the catalyst and a gas phase recycle system containing unreacted α-olefin, carbon monoxide, and hydrogen, or a combination of recycle systems.

When the hydroformylation process of this invention is conducted as described hereinabove, then the process produces two or more aldehydes with a target N/I ratio selectable over the range from 3 to 60 by controlling the carbon monoxide partial pressure. Such selection of the target N/I ratio over the range described hereinabove is advantageously achieved by employing the symmetric calixarene bisphosphite ligand of the present invention. Other advantages of the process of the present invention include: a) the process uses one bisphosphite ligand rather than a mixture of organophosphorus ligands as currently found in the art; and b) the bisphosphite ligand is symmetric, so as to facilitate rapid binding to the transition metal to form the transition metal-ligand complex catalyst.

Specific Embodiments

The following examples are illustrative of the present invention and are not to be regarded as limiting thereof. Based on the description and examples herein, variations in operational parameters, such as reactants, process conditions, species of transition metal-ligand complex catalyst, and symmetric calixarene bisphosphite ligands, falling within the scope of the claims will be apparent to those skilled in the art. All of the parts, percentages, and proportions referred to herein are given by weight, unless otherwise indicated.

The following examples illustrate the present invention by using the more preferred ligand, N,N-diethylacetamide-p-tert-butylcalix[4]arene bisphosphite, represented by formula (IV), which is reproduced here:

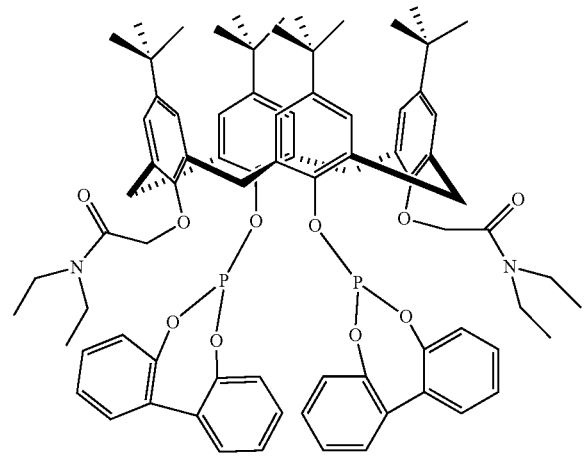

(IV)

EXAMPLES 1-7

These examples use 1-butene as an olefin feed, which is obtained from Aldrich Corporation (Batch No. 01622DC). Gas Chromatograph/Mass Spectrometry (GC/MS) analysis of this 1-butene olefin feed shows that it comprises the following GC observable components: 99.2 percent 1-butene, 0.4 percent trans-2-butene, 0.2 percent cis-2-butene and 0.2 percent isobutene, by weight calculated based on the weight of all the GC observable components.

A rhodium catalyst precursor (dicarbonylacetylacetonato rhodium (I), 0.008 g, 70 ppmw Rh) and the symmetric bisphosphite ligand of formula (IV) (0.085 g, 2 equivalents/Rh) are weighed into a septum-capped bottle in a dry box. The solids are dissolved in tetraglyme, and the resulting solution transferred via vacuum into a 100 ml Parr mini-reactor. The catalyst-containing solution is then preheated with agitation (1100 rpm) to 70° C. under 1:1 carbon monoxide: hydrogen (syngas) for 20-30 minutes. Liquid 1-butene olefin feed (9.2 ml, 5.5 g) is charged to an isolated section above the reactor, and pressured into the reactor with syngas. The desired pressure of 1:1 syn gas (corrected for olefin vapor pressure) is established with a Brooks model 5866 flow meter, and held constant throughout. Total gas uptake is measured with a Brooks 0151E totalizer. Liquid reaction samples are taken periodically and analyzed on an Agilent Technologies 6890 Gas Chromatograph (GC), equipped with a DB-1 30 m×0.32 mm, 1μ film column. FID chromatograms with integrated peak areas are obtained from the samples. The GC peak area percent exclusive of the solvent peak are used to quantify the peaks due to the unreacted α-olefin and the aldehyde products. Final conversion, N/I ratio and the iso-aldehyde selectivity are calculated using the GC data obtained from the final sample. Table 1 summarizes the reaction conditions and the GC analysis results of Examples 1-7.

TABLE 1

Reaction conditions and results of Examples 1-7.

| Example No. | CO (psi) | $H_2$ (psi) | Temperature (° C.) | Conv (Mol %) | Final N/I | Isoaldehydes Final (Mol %) |
|---|---|---|---|---|---|---|
| 1 | 257 | 257 | 85 | 66 | 4 | 21 |
| 2 | 257 | 257 | 70 | 23 | 7 | 12 |
| 3 | 107 | 107 | 70 | 37 | 15 | 6 |
| 4 | 57 | 57 | 70 | 53 | 22 | 4 |
| 5 | 32 | 32 | 70 | 60 | 31 | 3 |
| 6 | 17 | 17 | 70 | 68 | 50 | 2 |
| 7 | 12 | 12 | 70 | 68 | 51 | 2 |

The data in Table 1 illustrate that the rhodium complex catalyst of the symmetric calixarene bisphosphite of formula (IV) hydroformylates, under the conditions of these specific embodiments, 1-butene to yield two or more aldehydes with a target N/I ratio selectable in a range from 4 to 51 by changing the syngas pressure alone and the reaction temperature. The N/I range corresponds to an iso-aldehyde range of 2 mol % to 21 mol %, based on the total moles of each product.

EXAMPLES 8-14

These examples use 1-octene as an olefin feed, which is obtained from Aldrich Corporation (Batch No. 05125ME). Gas Chromatograph/Mass Spectrometry (GC/MS) analysis of this 1-octene olefin feed shows that it comprises the following GC observable components: 98.6 percent 1-octene, 0.4 percent cis- and trans-2-octene, 0.4 percent 1-decene, 0.2 percent 5-methyl-1-heptene, 0.1 percent cis- and trans-4-octene, 0.1 percent 3-methyl-2-heptene and 0.1 percent 1-hexene, by weight calculated based on the weight of all the GC observable components. 2-Methyl-1-heptene (the iso-olefin) is not detected.

A hydroformylation reaction is carried out for each example according to the general procedure described for Examples 1-7 hereinabove, except the following:
(a) 1-Octene olefin feed (3.6 g);
(b) Initial Rh concentration in each reaction solution is 100 ppmw (Rh(CO)$_2$acac, 0.011 g); and
(c) Reaction temperatures, hydrogen and carbon monoxide partial pressures are manipulated as shown in Table 2.

The results from GC analyses of the final samples from examples 8-14 (taken at 2 hours reaction time) are shown in Table 2.

TABLE 2

Reaction conditions and results of Examples 8-14

| Example No. | CO (psi) | $H_2$ (psi) | Temperature (° C.) | Conv (Mol %) | Final N/I | Isoaldehydes Final (Mol %) |
|---|---|---|---|---|---|---|
| 8 | 257 | 107 | 100 | 67 | 8 | 11 |
| 9 | 257 | 107 | 60 | 13 | 7 | 13 |
| 10 | 257 | 257 | 60 | 12 | 7 | 13 |
| 11 | 107 | 107 | 60 | 24 | 14 | 7 |
| 12 | 57 | 107 | 60 | 36 | 23 | 4 |

TABLE 2-continued

Reaction conditions and results of Examples 8-14

| Example No. | CO (psi) | $H_2$ (psi) | Temperature (° C.) | Conv (Mol %) | Final N/I | Isoaldehydes Final (Mol %) |
|---|---|---|---|---|---|---|
| 13 | 57 | 57 | 60 | 40 | 24 | 4 |
| 14 | 32 | 107 | 60 | 45 | 31 | 3 |

The data in Table 2 illustrate that the rhodium complex catalyst of the symmetric calixarene bisphosphite hydroformylates, under the conditions of these specific embodiments, 1-octene to yield two or more aldehydes with a target N/I ratio selectable in a range from 7 to 31 by changing the carbon monoxide partial pressure. Reaction temperature and hydrogen pressure have little or no effect on the N/I ratio of the two or more aldehydes. The N/I range corresponds to an iso-aldehyde range of 3 mol % to 11 mol %, based on the total moles of each product.

COMPARATIVE EXPERIMENTS 1-7

The symmetric bisphosphite, Ligand A mentioned in the Background, is used to carry out comparative experiments 1-7. The structure of Ligand A is reproduced here:

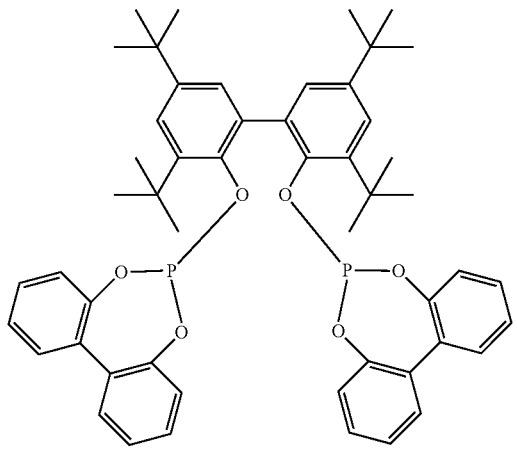

Ligand A

A hydroformylation reaction is carried out using Ligand A and the same 1-butene olefin feed as used in Examples 1-7 for Comparative Experiments 1-7 according to the general procedure described for Examples 1-7 hereinabove. Reaction temperatures, hydrogen and carbon monoxide partial pressures and results from GC analyses of the final samples from comparative examples (CEX) 1-7 (taken at 2 hours reaction time) are shown in Table 3.

TABLE 3

Reaction conditions and results of comparative experiments (CEX) 1-7

| CEX No. | CO (psi) | $H_2$ (psi) | Temperature (° C.) | Conv (Mol %) | Final N/I | Isoaldehydes Final (Mol %) |
|---|---|---|---|---|---|---|
| 1 | 257 | 257 | 85 | 85 | 32 | 3.0 |
| 2 | 257 | 257 | 70 | 60 | 29 | 3.3 |
| 3 | 107 | 107 | 70 | 80 | 51 | 1.9 |
| 4 | 57 | 57 | 70 | 83 | 69 | 1.4 |
| 5 | 32 | 32 | 70 | 75 | 59 | 1.7 |
| 6 | 17 | 17 | 70 | 67 | 42 | 2.3 |
| 7 | 12 | 12 | 70 | 67 | 23 | 4.2 |

The data in Table 3 illustrate that, under the set of reaction conditions, the rhodium complex catalyst of the symmetric bisphosphite Ligand A hydroformylates 1-butene to yield two or more aldehydes with an iso-aldehyde selectivity from 1.4 mol % to 4.2 mol %, based on the total moles of each product, which is much narrower than the iso-aldehyde selectivity of the symmetric calixarene bisphosphite of formula (IV) under a set of essentially identical reaction conditions.

COMPARATIVE EXPERIMENTS 8-12

The symmetric bisphosphite, Ligand B, mentioned in the Background, is used to carry out comparative experiments 8-12. The structure of Ligand B is reproduced here:

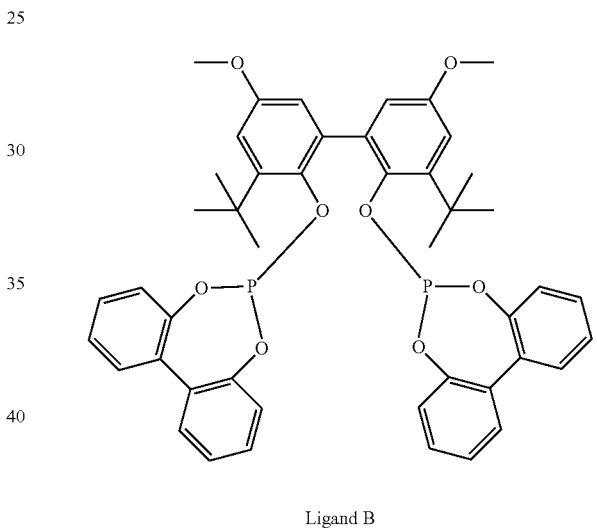

Ligand B

A hydroformylation reaction is carried out using Ligand B and the same 1-butene olefin feed as used in Examples 1-7 for Comparative Experiments 8-12 according to the general procedure described for Examples 1-7 hereinabove, except lower initial Rh concentration of 50 ppmw is provided with 0.006 g Rh(CO)$_2$acac. Reaction temperature, hydrogen and carbon monoxide partial pressures and results from GC analyses of the final samples from comparative examples (CEX) 8-12 (taken at 2 hours reaction time) are shown in Table 4.

TABLE 4

Reaction conditions and results of comparative experiments (CEX) 8-12

| CEX No. | CO (psi) | $H_2$ (psi) | Temperature (° C.) | Conv (Mol %) | Final N/I | Isoaldehydes Final (Mol %) |
|---|---|---|---|---|---|---|
| 8 | 107 | 107 | 50 | 55 | 92 | 1.1 |
| 9 | 57 | 57 | 50 | 67 | 61 | 1.6 |
| 10 | 32 | 32 | 50 | 72 | 165 | 0.6 |
| 11 | 17 | 17 | 50 | 74 | 199 | 0.5 |
| 12 | 12 | 12 | 50 | 73 | 213 | 0.5 |

The data in Table 4 illustrate that, under the set of reaction conditions, the rhodium complex catalyst of the symmetric bisphosphite Ligand B hydroformylates 1-butene to yield two or more aldehydes with an iso-aldehyde selectivity from 0.5 mol % to 1.1 mol %, based on the total moles of each product, which is even narrower than the iso-aldehyde selectivity of the symmetric bisphosphite Ligand A.

Embodiments of the Invention Include

1. A hydroformylation process for producing two or more aldehydes comprising a normal aldehyde and one or more iso-aldehydes with a target N/I ratio, which N/I ratio is defined as a molar ratio of the normal aldehyde to the iso-aldehydes, the process comprising contacting under reaction conditions an α-olefin represented by formula (I):

R—$CH_2$—CH=$CH_2$  (I)

wherein R is selected from the group consisting of hydrogen, substituted and unsubstituted $C_{1-9}$-alkyl moieties, with carbon monoxide and hydrogen in a reaction medium that is essentially free of an iso-olefin represented by formula (II):

R—$CH_2$—C($CH_3$)=$CH_2$  (II)

wherein R is as defined above, in the presence of a transition metal-ligand complex catalyst comprising a symmetric calixarene bisphosphite ligand represented by formula (III):

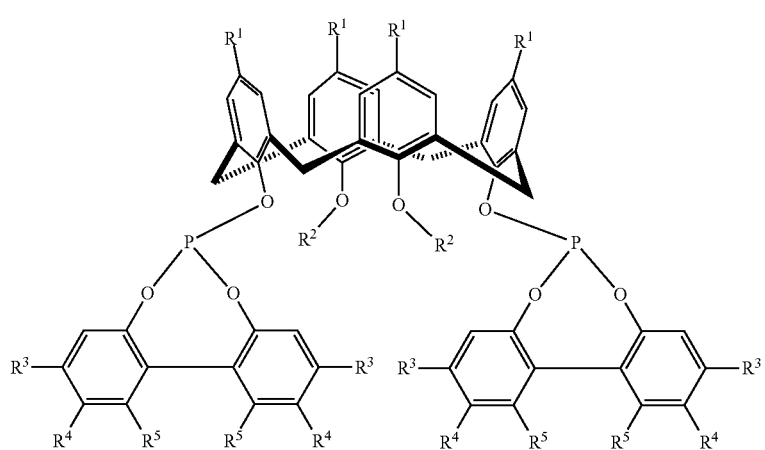

(III)

wherein each $R^1$ is the same and is selected from the group consisting of hydrogen and substituted or unsubstituted alkyl moieties;

wherein each $R^2$ is the same and is selected from the group consisting of substituted and unsubstituted alkyl, alkaryl, aralkyl, and amide moieties; and wherein each $R^3$ is the same, each $R^4$ is the same, and each $R^5$ is the same, and wherein $R^3$, $R^4$, and $R^5$ independently selected from hydrogen, alkyl, alkaryl, alkoxy, aryloxy, keto, carbonyloxy, and alkoxycarbonyl moieties;

which contacting occurs under a carbon monoxide partial pressure in a range from 6 psi (41 kPa) to 300 psi (2.1 mPa) to produce the two or more aldehydes with the target N/I ratio, which target N/I ratio is selectable over a range from 3 to 60 by controlling the carbon monoxide partial pressure.

2. Any one of the aforementioned embodiments wherein the target N/I ratio is preferably selected over a range from 4 to 60.
3. Any one of the aforementioned embodiments wherein the target N/I ratio is preferably selected over a range from 3 to 50.
4. Any one of the aforementioned embodiments wherein the target N/I ratio is preferably selected over a range from 4 to 50.
5. Any one of the aforementioned embodiments wherein the carbon monoxide partial pressure is preferably at least 12 psi (83 kPa) and less than 300 psi (2.1 mPa).
6. Any one of the aforementioned embodiments wherein the carbon monoxide partial pressure is preferably at least 6 psi (41 kPa), and less than 250 psi (1.7 mPa).
7. Any one of the aforementioned embodiments wherein the carbon monoxide partial pressure is preferably at least 12 psi (83 kPa), and less than 250 psi (1.7 mPa).
8. Any one of the aforementioned embodiments wherein each $R^1$ is the same and is preferably a $C_{1-20}$ alkyl.
9. Any one of the aforementioned embodiments wherein each $R^2$ is the same and is preferably selected from the group consisting of $C_{1-20}$ alkyl, $C_{7-20}$ alkaryl, and a amide represented by —$CH_2C(O)NR^6R^7$, wherein $R^6$ and $R^7$ are independently selected from substituted and unsubstituted $C_{1-15}$ alkyl moieties and $C_{6-25}$ aryl moieties.
10. Any one of the aforementioned embodiments wherein each $R^3$ is the same, each $R^4$ is the same, and each $R^5$ is the same, and wherein $R^3$, $R^4$, and $R^5$ are preferably independently selected from hydrogen, $C_{1-20}$ alkyl, $C_{7-20}$ alkaryl, $C_{1-20}$ alkoxy, $C_{6-20}$ aryloxy, —C(O)$R^8$, —C(O)O$R^8$ and —OC(O)$R^8$, wherein each $R^8$ is independently a substituted or unsubstituted $C_{1-15}$ alkyl or $C_{6-15}$ aryl moiety.
11. Any one of the aforementioned embodiments wherein each $R^1$ is the same and is preferably a $C_{1-20}$ alkyl, and wherein each $R^2$ is the same and is preferably selected from the group consisting of $C_{1-20}$ alkyl, $C_{7-20}$ alkaryl, and amide represented by —$CH_2C(O)NR^6R^7$, wherein $R^6$ and $R^7$ are independently selected from substituted and unsubstituted $C_{1-15}$ alkyl moieties and $C_{6-25}$ aryl moieties.
12. Any one of the aforementioned embodiments wherein each $R^1$ is the same and is preferably a $C_{1-20}$ alkyl, and wherein each $R^3$ is the same, each $R^4$ is the same, and each $R^5$ is the same, and wherein $R^3$, $R^4$, and $R^5$ are preferably independently selected from hydrogen, $C_{1-20}$ alkyl, $C_{7-20}$ alkaryl, $C_{1-20}$alkoxy, $C_{6-20}$ aryloxy, —C(O)$R^8$, —C(O)O$R^8$ and —OC(O)$R^8$, wherein each $R^8$ is independently a substituted or unsubstituted $C_{1-15}$ alkyl or $C_{6-15}$ aryl moiety 13. Any one of the aforementioned embodiments wherein each $R^2$ is the same and is preferably selected from the group consisting of $C_{1-20}$ alkyl, $C_{7-20}$ alkaryl, and a amide represented by —CH$_2$C(O)N$R^6R^7$, wherein $R^6$ and $R^7$ are independently selected from substituted and unsubstituted $C_{1-15}$ alkyl moieties and $C_{6-25}$ aryl moieties, and wherein each $R^3$ is the same, each $R^4$ is the same, and each $R^5$ is the same, and wherein $R^3$, $R^4$, and $R^5$ are preferably independently selected from hydrogen, $C_{1-20}$ alkyl, $C_{7-20}$ alkaryl, $C_{1-20}$alkoxy, $C_{6-20}$ aryloxy, —C(O)$R^8$, —C(O)O$R^8$ and —OC(O)$R^8$, wherein each $R^8$ is independently a substituted or unsubstituted $C_{1-15}$ alkyl or $C_{6-15}$ aryl moiety.

14. Any one of the aforementioned embodiments wherein each $R^1$ is the same and is preferably a $C_{1-20}$ alkyl, wherein each $R^2$ is the same and is preferably selected from the group consisting of $C_{1-20}$ alkyl, $C_{7-20}$ alkaryl, and an amide represented by —CH$_2$C(O)N$R^6R^7$, wherein $R^6$ and $R^7$ are independently selected from substituted and unsubstituted $C_{1-15}$ alkyl moieties and $C_{6-25}$ aryl moieties, and wherein each $R^3$ is the same, each $R^4$ is the same, and each $R^5$ is the same, and wherein $R^3$, $R^4$, and $R^5$ are preferably independently selected from hydrogen, $C_{1-20}$ alkyl, $C_{7-20}$ alkaryl, $C_{1-20}$alkoxy, $C_{6-20}$ aryloxy, —C(O)$R^8$, —C(O)O$R^8$ and —OC(O)$R^8$, wherein each $R^8$ is independently a substituted or unsubstituted $C_{1-15}$ alkyl or $C_{6-15}$ aryl moiety.

15. Any one of the aforementioned embodiments wherein the symmetric calixarene bisphosphite ligand is an N,N-diethylamide-p-tert-butylcalix[4]arene bisphosphite ligand represented by the following formula:

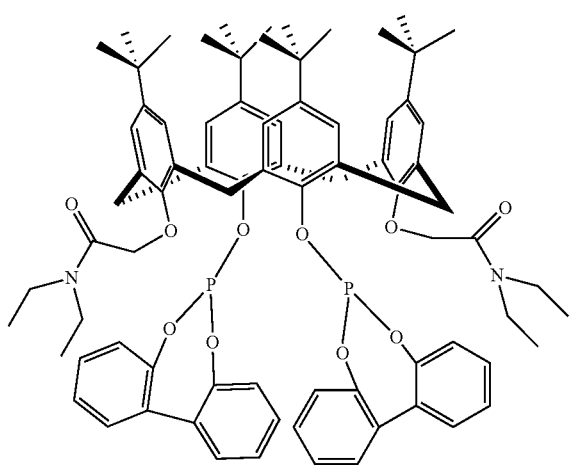

16. Any one of the aforementioned embodiments wherein the process is conducted in the presence of free symmetric calixarene bisphosphite ligand represented by formula (III).

17. Any one of the aforementioned embodiments wherein the transition metal is preferably selected from the group consisting of rhodium (Rh), cobalt (Co), iridium (Ir), ruthenium (Ru), iron (Fe), nickel (Ni), palladium (Pd), platinum (Pt), and osmium (Os), and mixtures thereof.

18. Any one of the aforementioned embodiments wherein the transition metal is more preferably selected from the group consisting of palladium, platinum, rhodium, cobalt, and iridium.

19. Any one of the aforementioned embodiments wherein the transition metal is still more preferably selected from the group consisting of rhodium and cobalt.

20. Any one of the aforementioned embodiments wherein the transition metal is most preferably rhodium.

21. Any one of the aforementioned embodiments wherein the concentration of the transition metal is advantageously greater than 10 parts per million by weight (ppmw) and less than 1,000 ppmw, calculated as free metal, based on the total weight of the hydroformylation reaction medium.

22. Any one of the aforementioned embodiments wherein the concentration of transition metal is preferably greater than 15 ppmw and less than 1,000 ppmw.

23. Any one of the aforementioned embodiments wherein the concentration of transition metal is preferably greater than 20 ppmw and less than 1,000 ppmw.

24. Any one of the aforementioned embodiments wherein the concentration of the transition metal is advantageously greater than 10 ppmw and less than 800 ppmw.

25. Any one of the aforementioned embodiments wherein the concentration of transition metal is preferably greater than 15 ppmw and less than 800 ppmw.

26. Any one of the aforementioned embodiments wherein the concentration of transition metal is preferably greater than 20 ppmw and less than 800 ppmw.

27. Any one of the aforementioned embodiments wherein the concentration of the transition metal is advantageously greater than 10 ppmw and less than 600 ppmw.

28. Any one of the aforementioned embodiments wherein the concentration of transition metal is preferably greater than 15 ppmw and less than 600 ppmw.

29. Any one of the aforementioned embodiments wherein the concentration of transition metal is preferably greater than 20 ppmw and less than 600 ppmw.

30. Any one of the aforementioned embodiments wherein the molar ratio of symmetric calixarene bisphosphite ligand to transition metal is greater than 1.0/1 and less than 100/1.

31. Any one of the aforementioned embodiments wherein the molar ratio of symmetric calixarene bisphosphite ligand to transition metal is greater than 1.2/1 and less than 100/1.

32. Any one of the aforementioned embodiments wherein the molar ratio of symmetric calixarene bisphosphite ligand to transition metal is greater than 1.5/1 and less than 100/1.

33. Any one of the aforementioned embodiments wherein the molar ratio of symmetric calixarene bisphosphite ligand to transition metal is greater than 1.0/1 and less than 50/1.

34. Any one of the aforementioned embodiments wherein the molar ratio of symmetric calixarene bisphosphite ligand to transition metal is greater than 1.2/1 and less than 50/1.

35. Any one of the aforementioned embodiments wherein the molar ratio of symmetric calixarene bisphosphite ligand to transition metal is greater than 1.5/1 and less than 50/1.

36. Any one of the aforementioned embodiments wherein the molar ratio of symmetric calixarene bisphosphite ligand to transition metal is greater than 1.0/1 and less than 10/1.
37. Any one of the aforementioned embodiments wherein the molar ratio of symmetric calixarene bisphosphite ligand to transition metal is greater than 1.2/1 and less than 10/1.
38. Any one of the aforementioned embodiments wherein the molar ratio of symmetric calixarene bisphosphite ligand to transition metal is greater than 1.5/1 and less than 10/1.
39. Any one of the aforementioned embodiments wherein the symmetric calixarene bisphosphite ligand and a transition metal source material are introduced into the reaction medium or zone, either separately or together, to form in situ the transition metal-ligand complex catalyst.
40. Any one of the aforementioned embodiments wherein the rhodium complex catalyst is prepared by the steps of:
    a) charging the symmetric calixarene bisphosphite, a rhodium source material, for example $Rh(CO)_2$acac, with a molar ratio of the symmetric calixarene bisphosphite to rhodium in a range described hereinabove, for example from 1.0/1 to 100/1, and an organic solvent into the reaction medium or zone, either separately or together, to form a mixture, and
    b) subjecting the mixture to reaction conditions to form the active catalyst.
41. Any one of the aforementioned embodiments wherein the reaction conditions sufficient for formation of the complex catalyst or catalyst precursor is substantially the same as the hydroformylation reaction conditions.
42. Any one of the aforementioned embodiments wherein the hydroformylation process employs advantageously an olefin feed that comprises primarily an α-olefin of formula (I) as defined hereinabove and is essentially free of an iso-olefin of formula (II) as defined hereinabove.
43. Any one of the aforementioned embodiments wherein the α-olefin is selected from the group consisting of propene, 1-butene, 1-pentene, 4-penten-1-ol, 1-hexene, 1-heptene, 1-octene, 1-nonene, 1-decene, 1-undecene, 1-dodecene, and methyl 10-undecenoate.
44. Any one of the aforementioned embodiments wherein the olefin feed comprises preferably at least 90% of the α-olefin by weight, based on the weight of the olefin feed.
45. Any one of the aforementioned embodiments wherein the olefin feed comprises more preferably at least 95% of the α-olefin by weight, based on the weight of the olefin feed.
46. Any one of the aforementioned embodiments wherein the olefin feed contains less than 0.4 weight percent of an iso-olefin of formula (II), based on the weight of the olefin feed, wherein the number 0.4 is not to be modified by the term "about."
47. Any one of the aforementioned embodiments wherein the olefin feed contains preferably less than 0.3 weight percent of an iso-olefin of formula (II), based on the weight of the olefin feed, wherein the number 0.3 is not to be modified by the term "about."
48. Any one of the aforementioned embodiments wherein the process is advantageously conducted at a temperature in a range from 60° C. to 110° C.
49. Any one of the aforementioned embodiments wherein the temperature is in a range from 65° C. to 110° C.
50. Any one of the aforementioned embodiments wherein the temperature is in a range from 60° C. to 100° C.
51. Any one of the aforementioned embodiments wherein the temperature is in a range from 65° C. to 100° C.
52. Any one of the aforementioned embodiments wherein each gaseous component of the hydroformylation process is preferably fed into the reactor independently at a target partial pressure and the carbon monoxide partial pressure is controlled by increasing or decreasing the carbon monoxide partial pressure, while keeping the partial pressures of hydrogen and the olefin feed within 90% of their respective target partial pressures.
53. Any one of the aforementioned embodiments wherein each gaseous component of the hydroformylation process is preferably fed into the reactor independently at a target partial pressure to obtain the two or more aldehydes with a target N/I ratio, which target N/I ratio is preferably selected by controlling the carbon monoxide partial pressure alone while keeping the partial pressures of other gaseous components within 95% of their respective target partial pressures.
54. Any one of the aforementioned embodiments wherein all gaseous components of the hydroformylation process are preferably fed into the reactor together to obtain the two or more aldehydes with a target N/I ratio, which target N/I ratio is preferably selected by controlling the total gas pressure of all the gaseous components while keeping the relative ratios of the gaseous components essentially unchanged, which effectively controls the carbon monoxide partial pressure in the reactor.
55. Any one of the aforementioned embodiments wherein the hydroformylation process is preferably carried out by using syngas to obtain the two or more aldehydes with a target N/I ratio, which target N/I ratio is preferably selected by controlling the syngas pressure, which effectively controls the carbon monoxide partial pressure in the reactor.
56. Any one of the aforementioned embodiments wherein the total gas pressure of all the gaseous components is preferably in a range from 15 psi (103 kPa) to 650 psi (4.5 mPa).
57. Any one of the aforementioned embodiments wherein the total gas pressure of all the gaseous components is preferably in a range from 30 psi (207 kPa) to 650 psi (4.5 mPa).
58. Any one of the aforementioned embodiments wherein the total gas pressure of all the gaseous components is preferably in a range from 15 psi (103 kPa) to 600 psi (4.1 mPa).
59. Any one of the aforementioned embodiments wherein the process is conducted at a total pressure in a range from 30 psi (207 kPa) to 600 psi (4.1 mPa).
60. Any one of the aforementioned embodiments wherein the molar ratio of gaseous hydrogen to carbon monoxide is preferably greater than 1/4 and less than 4/1.
61. Any one of the aforementioned embodiments wherein the molar ratio of gaseous hydrogen to carbon monoxide is preferably greater than 1/4 and less than 2/1.
62. Any one of the aforementioned embodiments wherein the molar ratio of gaseous hydrogen to carbon monoxide is more preferably greater than 1/4 and equal to or less than 1/1.
63. Any one of the aforementioned embodiments wherein the molar ratio of gaseous hydrogen to carbon monoxide is preferably greater than 1/2 and less than 4/1.
64. Any one of the aforementioned embodiments wherein the molar ratio of gaseous hydrogen to carbon monoxide is more preferably equal to or greater than 1/1 and less than 4/1.

65. Any one of the aforementioned embodiments wherein the process is preferably conducted using syngas under a syngas pressure in a range from 12 psi (83 kPa) to 600 psi (4.1 mPa).
66. Any one of the aforementioned embodiments wherein the syngas pressure is preferably in a range from 24 psi (166 kPa) to 600 psi (4.1 mPa).
67. Any one of the aforementioned embodiments wherein the syngas pressure is preferably in a range from 12 psi (83 kPa) to 500 psi (3.4 mPa).
68. Any one of the aforementioned embodiments wherein the syngas pressure is preferably in a range from 24 psi (166 kPa) to 500 psi (3.4 mPa).
69. Any one of the aforementioned embodiments wherein the process is conducted in the presence of a solvent selected from the group consisting of saturated hydrocarbons, aromatic hydrocarbons, ethers, aldehydes, ketones, nitriles, and aldehyde condensation products.
70. Any one of the aforementioned embodiments wherein the organic solvent is preferably a mixture that comprises primarily the aldehyde products desired to be produced in the process and higher boiling aldehyde liquid condensation by-products.
71. Any one of the aforementioned embodiments wherein the organic solvent is preferably any suitable solvent at the start-up of the process and eventually becomes a mixture comprising both aldehyde products and higher boiling aldehyde liquid condensation by-products.
72. Any one of the aforementioned embodiments wherein the process employs the solvent in an amount such that the solvent advantageously is more than 5 percent and less than 95 percent by weight, based on the total weight of the hydroformylation reaction medium.
73. Any one of the aforementioned embodiments wherein the amount of the solvent is preferably more than 10 percent and less than 95 percent by weight, based on the total weight of the hydroformylation reaction medium.
74. Any one of the aforementioned embodiments wherein the amount of the solvent is preferably more than 15 percent and less than 95 percent by weight, based on the total weight of the hydroformylation reaction medium.
75. Any one of the aforementioned embodiments wherein the amount of the solvent is preferably more than 5 percent and less than 90 percent by weight, of the total weight of the hydroformylation reaction medium.
76. Any one of the aforementioned embodiments wherein the amount of the solvent is preferably more than 10 percent and less than 90 percent by weight, based on the total weight of the hydroformylation reaction medium.
77. Any one of the aforementioned embodiments wherein the amount of the solvent is preferably more than 15 percent and less than 90 percent by weight, based on the total weight of the hydroformylation reaction medium.
78. Any one of the aforementioned embodiments wherein the process employs the solvent in an amount such that the solvent advantageously is more than 5 percent and less than 85 percent by weight, of the total weight of the hydroformylation reaction medium.
79. Any one of the aforementioned embodiments wherein the amount of the solvent is preferably more than 10 percent and less than 85 percent by weight, based on the total weight of the hydroformylation reaction medium.
80. Any one of the aforementioned embodiments wherein the amount of the solvent is preferably more than 15 percent and less than 85 percent by weight, based on the total weight of the hydroformylation reaction medium.

What is claimed is:

1. A hydroformylation process for producing two or more aldehydes comprising a normal aldehyde and one or more iso-aldehydes with a target N/I ratio, which N/I ratio is defined as a molar ratio of the normal aldehyde to the iso-aldehydes, the process comprising contacting under reaction conditions an α-olefin represented by formula (I):

$$R-CH_2-CH=CH_2 \quad (I)$$

wherein R is selected from the group consisting of hydrogen, substituted and unsubstituted $C_{1-9}$-alkyl moieties, with carbon monoxide and hydrogen in a reaction medium that is essentially free of an iso-olefin represented by formula (II):

$$R-CH_2-C(CH_3)=CH_2 \quad (II)$$

wherein R is as defined above, in the presence of a transition metal-ligand complex catalyst comprising a symmetric calixarene bisphosphite ligand represented by formula (III):

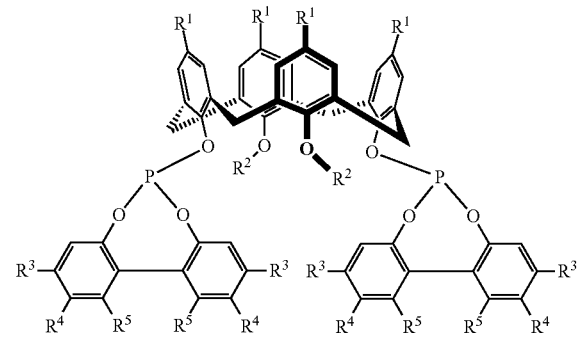

(III)

wherein each $R^1$ is the same and is selected from the group consisting of hydrogen and substituted or unsubstituted alkyl moieties;
wherein each $R^2$ is the same and is an amide moiety; and
wherein each $R^3$ is the same, each $R^4$ is the same, and each $R^5$ is the same, and wherein $R^3$, $R^4$, and $R^5$ are independently selected from hydrogen, alkyl, alkaryl, alkoxy, aryloxy, keto, carbonyloxy, and alkoxycarbonyl moieties;
which contacting occurs under a carbon monoxide partial pressure in a range from 6 psi (41 kPa) to 300 psi (2.1 mPa) to produce the two or more aldehydes with the target N/I ratio, which target N/I ratio is selectable over a range from 3 to 60 by controlling the carbon monoxide partial pressure.

2. The process of claim 1, wherein the symmetric calixarene bisphosphite ligand is an N,N-diethylamide-p-tert-butylcalix[4]Plarene bisphosphite ligand represented by the following formula:

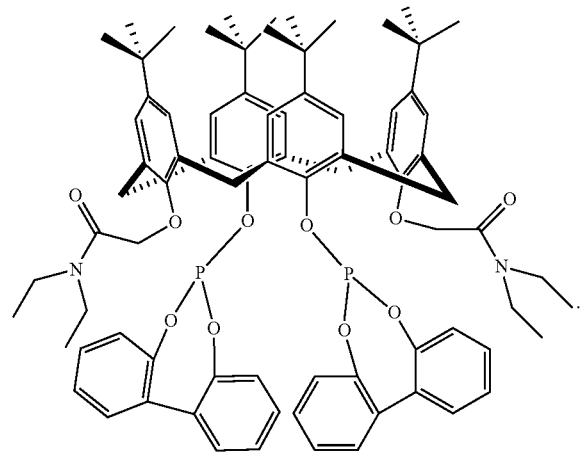

3. The process of claim 1, wherein the transition metal is rhodium.

4. The process of claim 1, wherein the process is conducted in the presence of free symmetric calixarene bisphosphite ligand represented by formula (III).

5. The process of claim 1, wherein the molar ratio of symmetric calixarene bisphosphite ligand to transition metal is greater than 1.0/1 and less than 100/1.

6. The process of claim 1, wherein the α-olefin is selected from the group consisting of propene, 1-butene, 1-pentene, 4-penten-l-ol, 1-hexene, 1-heptene, 1-octene, 1-nonene, 1-decene, 1-undecene, 1-dodecene, and methyl 10-undecenoate.

7. The process of claim 1, wherein the process is conducted at a temperature in a range from 60° C. to 110° C.

8. The process of claim 1, wherein the process is conducted under a total pressure in a range from 15 psi (103 kPa) to 650 psi (4.5 mPa).

9. The process of any one of claim 1, wherein the molar ratio of gaseous hydrogen to carbon monoxide is greater than 1/4 and less than 4/1.

10. The process of claim 1, wherein the process is conducted using syngas under a syngas pressure in a range from 12 psi (83 kPa) to 600 psi (4.1 mPa).

11. The process of claim 1, wherein the concentration of transition metal is greater than 10 parts per million by weight (ppmw) and less than 1,000 ppmw, calculated as free metal, based on the total weight of the hydroformylation reaction medium.

12. The process of claim 1, wherein the process is conducted in the presence of a solvent selected from the group consisting of saturated hydrocarbons, aromatic hydrocarbons, ethers, aldehydes, ketones, nitriles, and aldehyde condensation products.

13. The process of claim 1, wherein the solvent is more than 5 percent and less than 95 percent by weight, based on the total weight of the hydroformylation reaction medium.

14. The process of claim 2 wherein the transition metal is rhodium.

15. The process of claim 14 wherein the process is conducted at a temperature in a range from 60° C. to 110° C., wherein the process is conducted under a total pressure in a range from 15 psi (103 kPa) to 650 psi (4.5 mPa), wherein the molar ratio of gaseous hydrogen to carbon monoxide is greater than 1/4 and less than 4/1, and wherein the concentration of transition metal is greater than 10 parts per million by weight (ppmw) and less than 1,000 ppmw, calculated as free metal, based on the total weight of the hydroformylation reaction medium.

16. The process of claim 15, wherein the molar ratio of symmetric calixarene bisphosphite ligand to transition metal is greater than 1.0/1 and less than 100/1.

17. The process of claim 16, wherein the α-olefin is selected from the group consisting of propene, 1-butene, 1-pentene, 4-penten-l-ol, 1-hexene, 1-heptene, 1-octene, 1-nonene, 1-decene, 1-undecene, 1-dodecene, and methyl 10-undecenoate.

18. The process of claim 1 wherein $R^2$ is $-CH_2C(O)NR^6R^7$ wherein $R^6$ and $R^7$ are independently selected from substituted and unsubstituted $C_{1-15}$ alkyl and $C_{6-25}$ aryl moieties.

* * * * *